(12) United States Patent
Ha et al.

(10) Patent No.: US 7,459,307 B2
(45) Date of Patent: Dec. 2, 2008

(54) COMPOSITION FOR TREATMENT OF ARTICULAR CARTILAGE DAMAGE

(75) Inventors: Chul-Won Ha, 1-306, Misung Apartment, Apkujong-dong, Kangnam-ku, 135-785 Seoul (KR); Yoon-Sun Yang, Seoul (KR); Sung-Eun Yang, Seoul (KR)

(73) Assignees: Medipost Co., Ltd, Seoul (KR); Chul-Won Ha, Seoul (KR)

( * ) Notice: Subject to any disclaimer, the term of this patent is extended or adjusted under 35 U.S.C. 154(b) by 235 days.

(21) Appl. No.: 10/485,816

(22) PCT Filed: Aug. 14, 2002

(86) PCT No.: PCT/KR02/01552

§ 371 (c)(1),
(2), (4) Date: Apr. 5, 2004

(87) PCT Pub. No.: WO03/015802

PCT Pub. Date: Feb. 27, 2003

(65) Prior Publication Data

US 2004/0151703 A1    Aug. 5, 2004

(30) Foreign Application Priority Data

Aug. 14, 2001 (KR) ............................. 2001-49147
Aug. 14, 2001 (KR) ............................. 2001-49148

(51) Int. Cl.
*C12N 5/00* (2006.01)
*A01N 63/00* (2006.01)

(52) U.S. Cl. .................. 435/325; 424/93.1; 424/422

(58) Field of Classification Search ................. None
See application file for complete search history.

(56) References Cited

U.S. PATENT DOCUMENTS 5,902,741 A * 5/1999 Purchio et al. .............. 435/325
5,906,934 A   5/1999 Grande et al.

FOREIGN PATENT DOCUMENTS

EP     1099754      5/2001
WO     98/51317    11/1998

OTHER PUBLICATIONS

Radice M et al. 2000. Hyaluronan-based biopolymers as delivery for bone marrow-derived mesenchymal progenitors. J Biomed Mater Res 50: 101-109.*
Alejandro et al., "Mesenchymal progenitor cells in human umbilical cord blood", British Journal of Haematology, Oxford, GB, vol. 109, No. 1, Apr. 2000, pp. 235-242.
Wu Chengru et al., China Journal Surgery, Feb. 2001, vol. 39, No. 2, pp. 144-147 (indicated in Office Action as vol. 29).
Caplan et al., "Principles of cartilage repair and regeneration", Clinical Orthopaedics and Related Research, Sep. 1997, No. 342, pp. 254-269.
M.F. Pittenger et al., Science, vol. 284, Apr. 2, 1999, pp. 143-147.
H.M. Lazarus et al., Bone Marrow Transplantation, 1995, vol. 16, pp. 557-564.
F. Barry et al., Experimental Cell Research, 2001, vol. 268, pp. 189-200.
N. Jaiswal et al., Journal of Cellular Biochemistry, 1997, vol. 64, pp. 295-312.
S. Nehrer et al., Biomaterials, 1998, vol. 19, pp. 2313-2328.
P.L. Fitzpatrick et al., Aust. N.Z. J. Surg., 1998, vol. 68, pp. 573-579.
Cesare Campagnoli et al., "Identification of Mesenchymal Stem/Progenitor Cells in Human First-Trimester Fetal Blood, Liver, and Bone Marrow", Hematopoiesis, Blood, Oct. 15, 2001, vol. 98, No. 8, pp. 2396-2402.
Sarah A. Wexler et al., "Adult Bone Marrow Is A Rich Source of Human Mesenchymal 'Stem' Cells But Umbilical Cord and Mobilized Adult Blood Are Not", British Journal of Haematology, 2003 Blackwell Publishing Ltd., vol. 121, pp. 368-374.
Sekiya, I., et al., "In vitro cartilage formation by human adult stem cells from bone marrow stroma defines the sequence of cellular and molecular events during chondrogenesis," PNAS, 99:7, 4397-4402, Apr. 2, 2002.
Sekiya, I., et al., "Expansion of Human Adult Stem Cells from Bone Marrow Stroma: Conditions that Maximize the Yields for Early Progentiors and Evaluate Their Quality," Stem Cells, 20, 530-541, 2002.
Indrawattana, N., et al., "Growth factor combination for chondrogenic induction from human mescenchymal stem cell," Biochem. and Biophy. Research Comm., 320, 914-919, 2004.
Radice, M. et al., "Hyaluronan-based biopolymers as delivery vehicles for bone-marrow-derived mesenchymal progenitors," Institute of Histology and Embryology, Univ. of Padova, Padova, Italy, Clinic of Orthopedic and Trauma Surgery, Univ. of Padova, Padova, Italy, accepted Aug. 4, 1999; pp. 101-109.
Grande, D.A., et al., "Repair of Articular Cartilage Defects Using Mesenchymal Stem Cells," Tissue Engineering, vol. 1, No. 4, 1995, pp. 345-353.
Elisseeff, J., et al., "Transdermal photopolymerization for minimally invasive implantation," Proc. Natl. Acad. Sci. USA, vol. 96, Mar. 1999, pp. 3104-3107.
Saim, A.B., et al., "Engineering Autogenous Cartilage in the Shape of a Helix Using an Injectable Hydrogel Scaffold," The Laryngoscope, 110, Oct. 2000, pp. 1694-1697.
Grande, D.A., et al., "Cartilage Tissue Engineering: Current Limitations and Solutions," Clinical Orthopaedics and Related Research, No. 367S, 1999, pp. S176-S185.
Von der Mark, K., et al., "Relationship between cell shape and type of collagen synthesised as chondrocytes lose their cartilage phenotype in culture," Nature, vol. 267, Jun. 9, 1977, 531-532.
Benya, P.D., et al., "Dedifferentiated Chondrocytes Reexpress the Differentiated Collagen Phenotype When Cultured in Agarose Gels," Cell, vol. 30, Aug. 1982, pp. 215-224.

* cited by examiner

*Primary Examiner*—Lora E Barnhart
(74) *Attorney, Agent, or Firm*—Sughrue Mion, PLLC

(57) ABSTRACT

Disclosed herein is a composition for the treatment of articular cartilage damage or loss or defect. The composition for the treatment of articular cartilage injury of the present invention includes (i) cellular components separated, proliferated, and/or differentiated from the umbilical cord blood, (ii) a culture medium; and (iii) a biocompatible polymer. The composition has very superior ability of proliferation and differentiation and easier to be collected and acquired.

33 Claims, 3 Drawing Sheets
(3 of 3 Drawing Sheet(s) Filed in Color)

[FIG. 1]
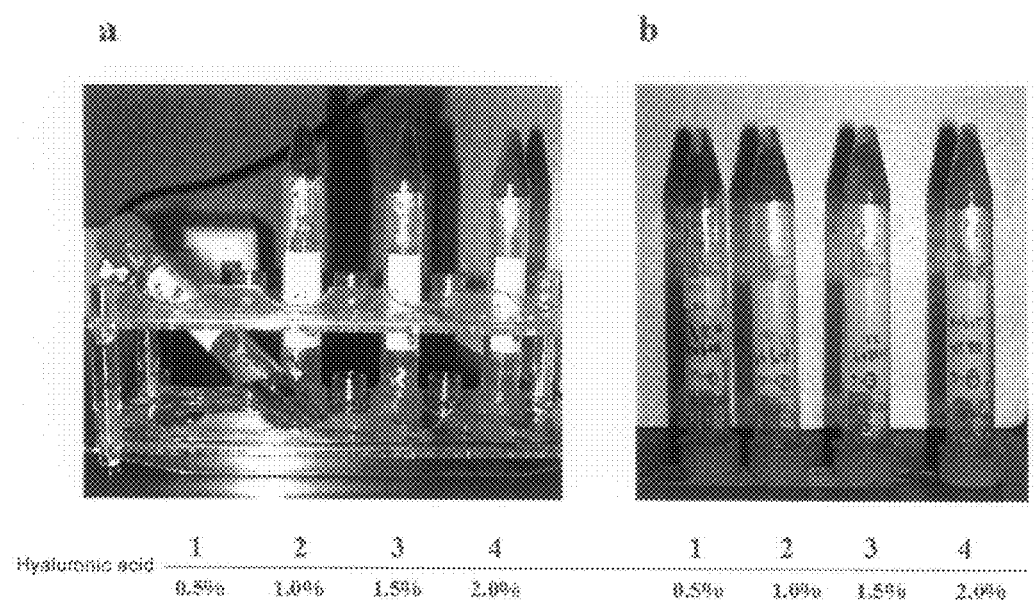

[FIG. 2]
a
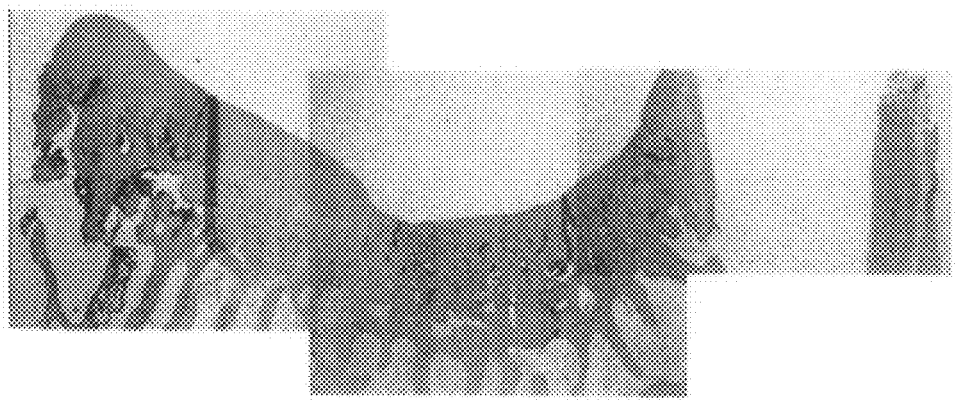
b
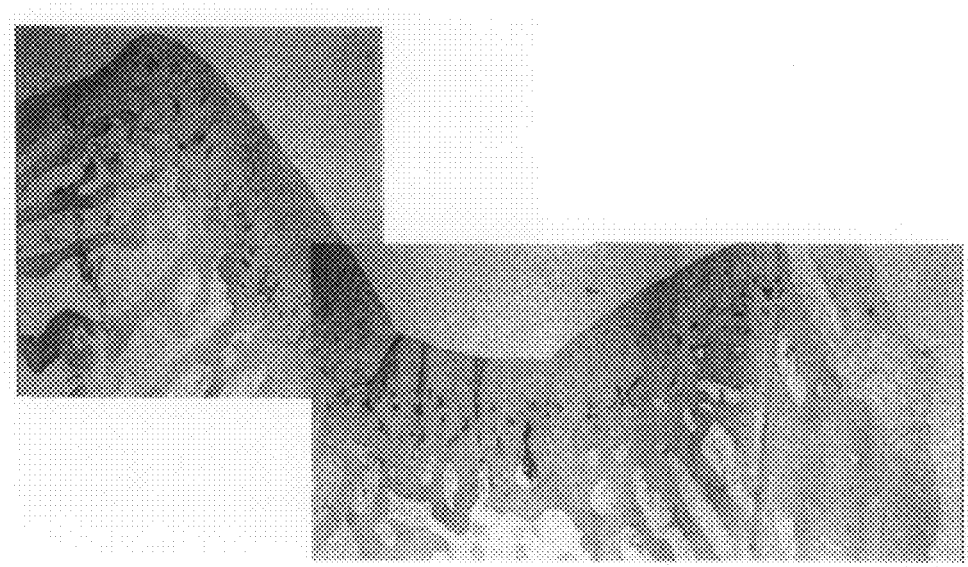

[FIG. 3]
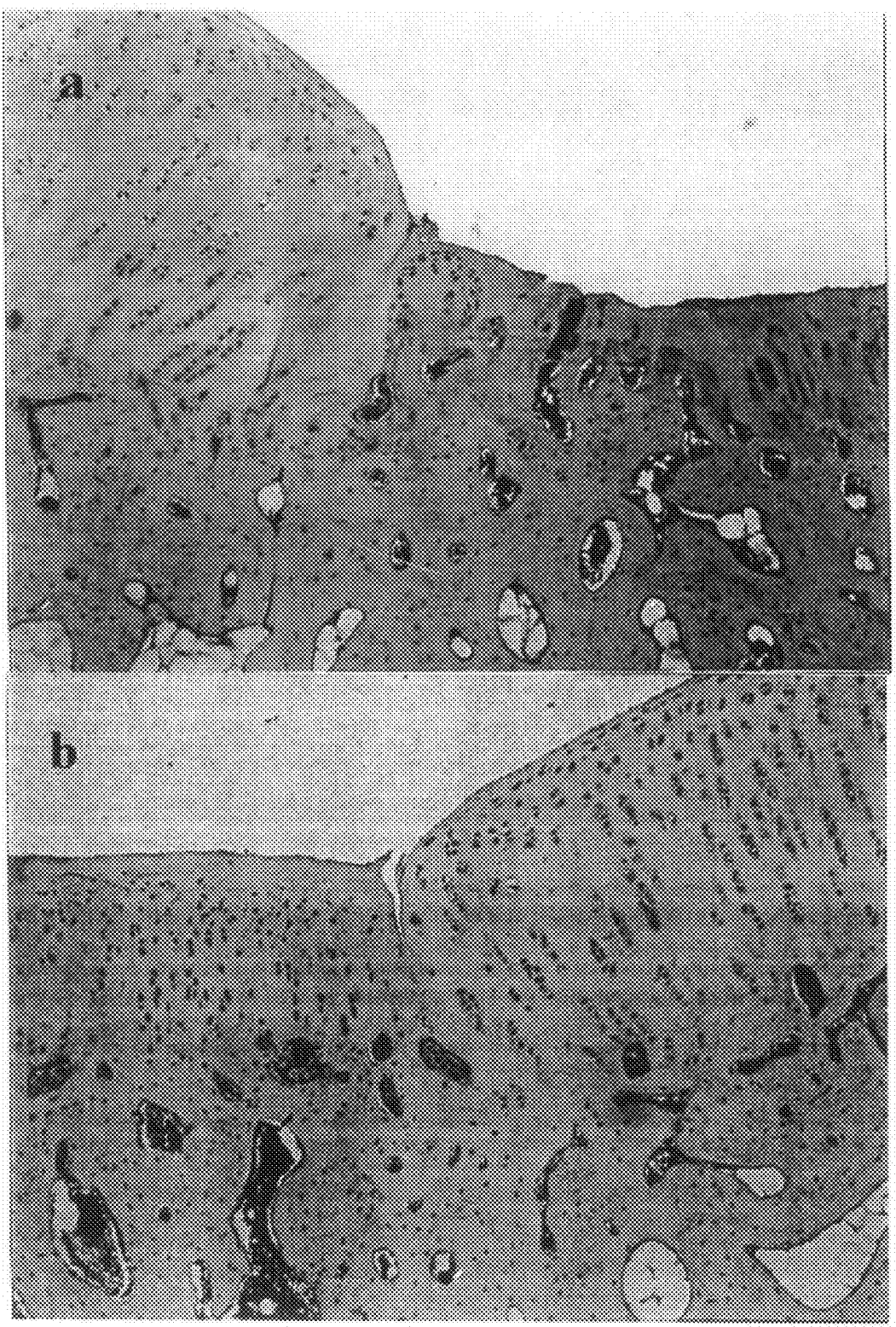

COMPOSITION FOR TREATMENT OF ARTICULAR CARTILAGE DAMAGE

This is a National Stage application under 35 U.S.C. § 371 of PCT/KR02/01552 which claims benefit of Korean Patent Applications 2001/49147 and 2001/49148 filed on Aug. 14, 2001, all of which are incorporate herein by reference.

BACKGROUND OF THE INVENTION

1. Field of the Invention

The present invention is related to a composition for the treatment of articular cartilage damage or loss or defect.

2. Description of the Prior Art

The articular cartilage damage induces pain in the articular region, fault of the articular movement, etc., and lowers the quality of life as well as productivity. Particularly, it is difficult to treat completely the articular cartilage damage since the natural healing power is very low and it is connected to the damage to the entire articulation as it is progressed continuously once it occurs.

The methods of treatment of articular cartilage damage developed up to the present time include chondroplasty, osteochondral, transplantation, autologous chondrocyte transplantation, etc.

Chondroplasty is the most generally used method among the above-described methods. The arthroscopic operation which is the representative method is a method in which diagnosis and operation may be performed simultaneously while magnifying and observing inside of the articulation through a TV monitor by inserting an arthroscope, on which a small-sized camera is mounted, into the articular cavity through a small hole of less than 1 cm.

The above method is advantageous in that it is possible to reduce pain and burden of a patient since it is not necessary to have a direct incision of articulation and it is possible to cure immediately after minor damages to tissues are observed through the arthroscope. However, this chondroplasty is not satisfactorily effective in view of its functional aspects since the fibro-cartilage, not hyaline cartilage that is necessary for the articulation actually, is produced mainly.

In the meantime, osteochondral transplantation is a method of producing hyaline cartilage by collecting both of the cartilage and sub-cartilage portions produced already in the normal section of a patient and transplanting them in the damaged cartilage section by making holes properly. This method has been successful in some patients. However, this method may not be said to be a perfect treatment method because of a problem of having cracks between the transplanted portion and original tissues, and is not a general method in that it may be applied to only the patients who are able to be subject to autologous transplantation. And the above method may not be operated if the damaged portion is large since the donated portion is limited, and it is likely that complications occur in the donated portion. Also, the process of operation is comparatively complicated, and sometimes it is not possible to perform arthroscopic operation. In other words, the above method has weaknesses such as a new pain in the donated portion and may incur complications such as a slow rehabilitation including pain, fracture, bleeding, and scar after operation.

Autologous chondrocyte transplantation that has been started to be employed recently is a method of filling the cartilage portion damaged by proliferation of these cells by obtaining chondrocytes from cartilage tissues collected from the normal portion of a patient, culturing and growing them as much as they are needed externally, securing a space by using periosteum and injecting them to the damaged portion of cartilage along with the culture medium.

Compared to the osteochondral transplantation method in which already produced cartilage tissues are injected to the damaged portion, there is a more possibility of reproducing hyaline cartilage as the transplanted portion is fused comparatively well with the normal portion since the damaged portion is filled with transplanted chondrocytes as they are proliferated directly in the damaged portion. However, there are still pain, after effects, and economical burden of a patient eventually due to the operation of twice and the process of operation is also complicated and difficult since it is necessary to perform operation when collecting chondrocytes and when transplanting those cultured externally are transplanted to the portion of articular cartilage damage.

And there are problems with chondrocytes in that it takes a considerable amount of time until as much as the cells that are necessary for transplantation during external culturing of cells are obtained as the proliferation and growth of the, cells collected are not active since the chondrocytes collected are obtained from fully grown adults in most cases; the treatment itself could not be accomplished if the cells lose the ability to proliferate at all; and the form of expression of cells is changed since chondrocytes are cultured externally. And it is of concern that the life of cartilage made by culturing again fully grown cells would not be long. And in case of the second operation, complications such as pain, scar, etc. after operation are inevitable since it is necessary to perform a serious incision since no arthroscopic operational methods have been developed yet.

It has been reported that there has been a method of obtaining mesenchymal stem cells (MSCs) that are precursor cells of chondrocytes and osteoblasts from mesenchymal tissues such as autologous bone marrows, muscles, skin, etc., proliferating them ex vivo, and injecting them into the portion of articular cartilage damage together with polymers.

It is shown that the cell proliferation ability in the method of treatment of cartilage damage by using mesenchymal stem cells obtained from grown individuals as described in the above is somewhat higher than that of the autologous chondrocyte transplantation method since more undifferentiated cells are obtained and cultured ex vivo. However, the above-described method still shows a weak ability to proliferate cells for the treatment of various ways of cartilage damage fully. Also, the above-described method is required to have a difficult process of collection of bone marrows, and is limited in that construction of an infrastructure such as bone marrow storage banks, etc. is weak.

As described in the above, the methods of treatment of articular cartilage damage developed up to the present time have been problematic in view of their operational processes and effects.

SUMMARY OF THE INVENTION

It is therefore an object of the present invention to provide a composition for the treatment of articular cartilage damage or loss or defect composed of cellular components separated, proliferated, and/or differentiated from the umbilical cord blood, and biocompatible polymers that can have superior effects of treatment of articular cartilage damage through relatively simple operations.

The composition for the treatment of articular cartilage damage of the present invention is characterized by that it is composed of cellular components separated, proliferated, and/or differentiated from the umbilical cord blood, and their media. Another composition for the treatment of articular cartilage damage or loss or defect of the present invention is characterized by that it is composed of the above cellular components, their media, and biocompatible polymers. Still another composition for the treatment of articular cartilage damage or loss or defect of the present invention is characterized by that it is composed of cellular components separated or differentiated from the umbilical cord blood, and biocompatible polymers.

The cellular components of the composition for the treatment of articular cartilage damage or loss or defect of the present invention are one or more cellular components such as mesenchymal stem cells and/or mesenchymal stern/progenitor cells separated and/or cultured from the umbilical cord blood, precursor cells that are differentiated from the above mesenchymal stem cells and/or stem/progenitor cells, chondrocytes and/or osteoblasts that are differentiated from the above umbilical cord blood-derived mesenchymal stern/progenitor cells.

In the composition for the treatment of articular cartilage damage of the present invention, the umbilical cord blood which is the originating tissue of cellular components is defined to be the blood collected from the umbilical vein connecting placenta and fetus.

Among the cellular components of the composition for the treatment of articular cartilage damage of the present invention, mesenchymal stem cells separated from the umbilical cord blood may be differentiated into mesenchymal tissues such as bones, cartilage, fatty tissues, muscles, tendon, etc. under proper conditions for differentiation since they are multipotent contrary to typical stromal cells of bone marrows. Also, mesenchymal stem cells originated from the umbilical cord blood are the cells that may be proliferated under proper conditions without being differentiated into specific cells or tissues since they have the ability to self-renewal.

Among the cellular components of the composition for the treatment of articular cartilage damage of the present invention, precursor cells include all those that may be obtained during the process of differentiation of mesenchymal stem cells of the umbilical cord blood into chondrocytes or osteocytes, chondroblasts, osteoblasts, etc. among the cells originated from mesenchymal stem cells of the umbilical cord blood.

The cellular components of the composition for the treatment of articular, cartilage damage of the present invention may have a much superior ability to proliferate and differentiate since they are the cells originated from younger cells compared to the cells originated from cells including mesenchymal stem cells separated from adult tissues such as bone marrows, muscles, skin, etc.

In the collection and acquisition of originating tissues of the cellular components of the composition for the treatment of articular cartilage damage of the present invention, it is much easier to collect the cellular components than to collect cells from adult tissues such as bone marrows, etc. that require for operative procedures.

Moreover, it is easy to find a donor for the umbilical cord blood since banking or storing of umbilical cord blood is more feasible at birth and the stored umbilical cord blood can be used easily after thawing. Routine storing of bone marrow like umbilical cord blood is impossible.

And since the cellular components of the composition for the treatment of articular cartilage damage of the present invention are the cells of which major histocompatibility antigen HLA-DR (Class II), which is the most important cause of rejection reaction in interpolation or organ transplantation, is not expressed, the autologous umbilical cord blood as well as allogenic umbilical cord blood may be used in that it is possible to avoid bringing about or minimize immune reactions such as rejection reaction, etc. that may be the problem of the conventional transplantation operation.

The media of the composition for the treatment of articular cartilage damage of the present invention is for suspending cellular components. Generally used cell culture media such as McCoys 5A media (Gibco), Eagle's basal media, CMRL media, Glasgow minimum essential media, Ham's F-12 media, Iscove's modified Dulbecco's media, Liebovitz' L-15 media, RPMI 1640 media, etc. may be used.

In the present invention, if necessary, one or more secondary components may be added to the cell culture media. That is, one or more components selected from the sera of a fetal calf, horse, human, etc.; antibiotics such as Penicillin G, gentamycin, streptomycin sulfate, etc. for preventing contamination of microorganisms; antifungal agents such as amphotericin B, nystatin, etc. may be used.

Biocompatible polymers of the composition for the treatment of articular cartilage damage of the present invention are characterized by having one or more characteristics among the biocompatibility, biodegradation property and ability to enhance nutrition of cells and ability to enhance formation of intercellular substrate. Biocompatible polymers of the composition for the treatment of articular cartilage damage of the present invention have the semi-solid or gel-like property to the degree that is similar to that of ointments or pastes as well as the mechanical strength and flexibility to the degree that are proper for cellular transplantation and regeneration of cartilaginous tissues or bone.

Accordingly, the composition for the treatment of articular cartilage damage of the present invention is able to accelerate proliferation and differentiation of chondrocytes that are transplanted together as it is located at the damaged region, continuously while maintaining a constant shape once it is transplanted and seeking for convenience in operation since its shape may be changed readily to conform to various 3-dimensional geometry that may be shown in the damaged region of cartilage.

Biocompatible polymers that may be used for the composition for the treatment of articular cartilage damage of the present invention may be one or more components selected from natural polymers such as proteins, polysaccharides, etc; synthetic polymers comprised of hydroxy acids or their derivatives; and organic polymers forming the 3-dimensional scaffold or lattice structure according to chemical binding and their derivatives and transformed compounds. For example, the proteins among natural polymers include fibrin, gelatin, and collagen; saccharides among natural polymers include hyaluronic acid, etc.; synthetic polymers include polyphosphazine, polyacrylate, polyglactic acid, and polyglycolic acid; and organic polymers include pluronic acid, alginic acid and its salts, etc.

It is possible to promote the mechanical strength and flexibility of the composition for the treatment of articular cartilage damage of the present invention by adding the chitosan fiber.

If a polymer is used singly in the present invention, it is possible to adjust its concentration according to the molecular weight and characteristics of each polymer component. The final content of pluronic acid after it is mixed with cells when it is used singly is 30%, and it is preferable to make the final content of hyaluronic, acid 3-4% after it is mixed with cells when it is used alone.

When using polymers mixedly in the present invention, it is preferable to use those that are made by mixing them in such a way that the final content of pluronic acid after it is mixed with cells is 15-30% and the final content of hyaluronic acid is 2-4%.

If the chitosan fiber is added to the mixed polymer of the above pluronic acid and hyaluronic acid in the present invention, it is preferable to add and mix the same amount of the chitosan fiber to and with the above mixed polymer.

Illustrated below are the method of manufacture of the composition for the treatment of articular cartilage damage and the method of treatment of articular cartilage damage using the above of the present invention.

The method of manufacture of the composition for the treatment of articular cartilage damage of the present invention is comprised of the steps of collection of the umbilical cord blood; separation, culturing, and/or differentiation of mesenchymal stem cells from the umbilical cord blood; and mixing those mesenchymal stem cells and polymers. Each step is further described in detail as follows:

In the step of collection of the umbilical cord blood, in case of the normal vaginal delivery, the umbilical cord blood is collected from the umbilical vein that is extracted fully to the outside in a state that the placenta remains in the uterus after childbirth, or from the umbilical vein in a state that the placenta is extracted fully from the uterus also after childbirth in case of cesarean section.

When collecting the umbilical cord blood from the umbilical vein extracted fully to the outside of the uterus after childbirth in the present invention, it is collected from the umbilical vein connecting the placenta and fetus after a infant is born according to aseptis, where both methods of collecting the umbilical cord blood before the placenta is removed in the uterus after childbirth and of collecting the umbilical cord blood externally after the placenta is removed may be used. After the umbilical vein is secured, the umbilical cord blood is collected in a collection bag containing an anticoagulant by using collection needles.

All conventional methods including that in Korean Patent Application No. 10-2002-0008639, and those in Pittinger M F, Mackay A M, et al. Science 1999; 284: 143-7, Lazarus H M, Haynesworth S E, et al., Bone Marrow Transplant 1995; 16: 557-64 may be used for the method of separation and culturing of mesenchymal stem cells and mesenchymal stem/progenitor cells from the umbilical cord blood collected as described in the above. Among them, an example is described as follows:

Mononuclear cells are separated through centrifugal separation of the umbilical cord blood and washed several times in order to remove foreign materials. If they are plated and cultured in a culture dish and/or flask and/or other container after they are washed, cells are proliferated with forming monolayer. Among them, mesenchymal stem cells and/or stem/progenitor cells are those of which shape observed through a inverted microscope is homogeneous and that are proliferated in the form of colonies of long cells of the spindle shape. Thereafter, when the cells are grown to be confluent, sub-culturing is performed in order to have the cells proliferated until the necessary number of cells is reached.

Mesenchymal stem cells and stem/progenitor cells originated from the umbilical cord blood of the present invention may be used directly for the operation or after they go through the differentiation process.

As to the method of differentiation of mesenchymal stem cells originated from the umbilical cord blood of the present invention, any proper method in which desired cells may be obtained may be selected and used among conventionally used methods (Barry F, Boynton R E, et al., Exp cell Res 2001; 268: 189-200, Jaiswal N, Haynesworth S E, et al., J Cell Biochem 1997; 64: 295-312). Among them one example is described as follows:

While culturing cells originated from the umbilical cord blood in proper chondrogenic differentiation media or osteogenic differentiation media, to what degree differentiation is progressed is confirmed through the measurement of expression of enzymes, immune expression type analysis, histochemical stain, histoimmunologic stain, molecular biological examination, or cellular medium analysis. Mesenchymal stem cells thus manufactured and the cells differentiated from then may be used directly for the operation, or may be kept frozen, thawed when necessary, and proliferated again to be used.

The method of keeping the cells of the present method frozen is performed according to the widely known method (Doyle et al., 1995). The medium used for keeping frozen is composed of 10-20% FBS (fetal bovine serum), 10% DMSO (dimethylsulfoxide), and 5-10% glycerol. The cells are suspended in such a way that about $1 \times 10^6$ to $5 \times 10^6$ cells exist in 1 ml of the above medium.

The above suspension of cells is distributed into glass or plastic amples for low-temperature freezing, sealed, and put into a controlled rate freezer with the conditions for temperature adjusted in advance. It is preferable to use a freezing program offering the change of temperature of $-1°$ C./min when freezing the cells since it is possible to reduce damage to the cells when they are thawed thereafter. Once the temperature of amples reaches $-180°$ C., they are transferred to a liquid nitrogen storage tank. The cells kept frozen may be stored for several years. Whether the viability of the cells is maintained should be checked periodically at least every five years. When thawing the cells kept frozen, the amples are moved promptly to a water tub of which temperature is adjusted to $37°$ C. from the liquid nitrogen storage tank. The content thawed in the amples is moved immediately to a culturing container having the medium containing 10% FBS and 5% ES in the sterilized state. The density of cells on the culturing medium is adjusted to have about $3 \times 10^5$ to $6 \times 10^5$ cells existed per ml of the medium. Whether the cells are proliferated is checked with a inverted microscope every day. When a proper density of cells is reached, the cells are transferred to a new medium for sub-culturing.

The cells cultured as described in the above are transplanted directly to the region of articular cartilage damage in the state suspended on a proper medium or after they are mixed with polymers. In other words, a method of injection of the cells suspended on the medium to a space made of appropriate biomembranes such as periosteum, etc. of the region of cartilage damage in a state not mixed with polymers, sealing them so that the suspension of cells is not leaked out through the cracks of this periosteum, and suturing all of incised sections of operation may be used. Or the above cells may be used by mixing them with appropriate polymers along with the medium and making them in a state which is similar to that of ointments or pastes. In all cases, it is preferable to adjust the concentration of cells contained finally in the composition of the present invention to have $1 \times 10^6$ to $5 \times 10^7$ cells existed in 1 ml. The amount of administration of the composition of the present invention may be increased or reduced according to the size of the portion of articular damage to be cured, and generally, it is preferable to use about 2 ml in case of knee joints of adults having the size of about 2 cm$^2$.

In the method of treatment of the articular cartilage damage using the composition of the present method, the articular cartilage portion to be operated is observed preferably through the arthroscopic operation, the damaged portion is prepared to facilitate the operation, the composition of the present invention is applied to the damaged portion, and whether it is positioned stably is confirmed preferably by using an arthroscope. The form of the composition of the present invention may be formulated to fit into the damaged portion in advance before it is applied to the lesion or changed to fit after it is applied into the damaged portion.

As described above, the method of treatment of the articular cartilage damage using the composition of the present invention may secure the convenience of the procedures and reduce pain, sequelae and morbidity of a patient since the damaged cartilage may be cured sufficiently through, the arthroscopic operation, whereas conventional cell plantation methods require for the operation of several times.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee The foregoing and other objects, aspects, and advantages will be better understood from the following detailed description of a preferred embodiment of the invention with reference to the drawings, in which:

FIGS. 1a and 1b are the diagrams in which the viscosity and strength of a polymer manufactured by mixing pluronic acid and hyaluronic acid, and that manufactured by mixing the chitosan fiber, pluronic acid, and hyaluronic acid are confirmed;

FIGS. 2a and 2b are the diagrams showing the results of treatment of the portion of articular cartilage damage of rabbits by using the composition of the present invention; and FIGS. 3a and 3b are the diagrams showing the amplified portion of cartilage produced newly by the composition of the present invention.

DETAILED DESCRIPTION OF A PREFERRED EMBODIMENT OF THE INVENTION

Hereinafter, the present invention is illustrated in more detail in a preferred embodiment of the invention. However, the scope of the present invention is not limited by that preferred embodiment and it could be changeable for human application.

Referring now to the drawings, illustrated in the following preferred embodiment are the methods of manufacture of the composition of the present invention and of treatment of the articular cartilage damage using the above.

Firstly, cellular components are separated and cultured as follows in order to manufacture the composition of the present invention:

Mononuclear cells are separated through centrifugal separation of the umbilical cord blood and washed several times in order to remove foreign materials. If they are plated and cultured in a culture dish and/or flask and/or other container after they are washed, cells are proliferated with forming monolayer. Among them, mesenchymal stem cells and/or stem/progenitor cells are those of which shape observed through a inverted microscope is homogeneous and that are proliferated in the form of colonies of long cells of the spindle shape. Thereafter, when the cells are grown to be confluent, sub-culturing is performed in order to have the cells proliferated until the necessary number of cells is reached.

Mesenchymal stem cells and/or stem/progenitor cells of the umbilical cord blood obtained as described in the above are treated with trypsin, washed, suspended on a DMEM medium, and prepared for so that they may be mixed with the polymer in subsequent steps.

Secondly, for the manufacture of the composition of the present invention, polymers are prepared as follows and chemical, biological and/or mechanical properties of polymers are confirmed by performing experiments confirming their chemical, biological and/or mechanical strength in advance.

In order to confirm the mechanical strength according to the concentration or addition or reduction of the components comprising polymers, a polymer containing 30% of pluronic acid finally, a polymer containing 4% of hyaluronic acid finally, a polymer containing hyaluronic acid of each different concentration while containing 15% of pluronic acid finally, and a polymer containing the mixture of the above pluronic acid and hyaluronic acid and further containing the same amount of the chitosan fiber are prepared, in which the final concentrations of hyaluronic acid are 0.5%, 1.0%, 1.5%, 2.0% and 4.0%, respectively.

Each polymer is prepared by mixing the above components and whether each has the proper/appropriate property is evaluated.

As a result, as shown in FIG. 1a, a fairly good mechanical strength is shown in case of the polymer containing hyaluronic acid of each different concentration while containing 15% of pluronic acid finally. But it is seen that the mechanical strength is lowered as the concentration of hyaluronic acid is lowered. Particularly, it is observed that the polymer flows down along the wall of the tube if the tube is held upside down when less than 0.5% of hyaluronic acid is contained finally as the mechanical strength is lowered significantly.

On the other hand, the polymer containing the mixture of the above pluronic acid and hyaluronic acid and additionally the same amount of the chitosan fiber shows the flexibility of the degree which is good to change the shape when it is applied to the damaged region while maintaining the mechanical shape irrespective to the amount of hyaluronic acid. The polymer containing 30% of pluronic acid finally also shows proper mechanical strength and flexibility.

Accordingly, it is possible to select a polymer having the appropriate strength and flexibility to the degree which is proper for applying to the treatment of the region of cartilage damage and its mixed composition.

Thirdly, in order to manufacture the composition of the present invention, among the polymers manufactured in the above, for example, a polymer containing 30% of pluronic acid finally is selected, of which 0.3 g is mixed with about 0.9 ml of the DMEM medium sufficiently. Thereafter, the suspension of cells in the first step in which $1 \times 10^7$ cells are contained is concentrated in terms of centrifugal separation, the supernatant is discarded, and the polymer made in the second step is put into the cell portion only. A proper amount of the medium is then added to the above to make the final volume of 1 ml. That is, the composition for the treatment of articular cartilage damage of the present invention is manufactured to include 30% (0.3 g) of the polymer and $1 \times 10^7$ cells in 1 ml of the medium. If the amount becomes greater, they are mixed at the same ratio.

Fourthly, the articular cartilage damage is treated by using the composition for the treatment of articular cartilage damage of the present invention.

In order to design models for the articular cartilage damage, a healthy rabbit is selected and proper amounts of ketamine (35 mg/kg) and xylazine (5 mg/kg) according to its body weight are injected intramuscularly. After it is confirmed that the anesthesia of the rabbit is completed fully, the knee joints of both legs are shaved and fixed with an adhesive plaster while maintaining the supine posture. Both knee joints are disinfected with betadine, their locations are confirmed by palpation with fingers, after which the inside of the joint is observed by reaching the inside of knee joints through the paramedian approach along the incision line passing through the upper and lower portions of knee joints and inner side of the knee cap and bending the knee joints while pushing the knee cap toward the outer side.

After it is confirmed that there are no particular pathologic findings, a centralizing dimple is made at a position 4 mm above the front upper end of the central interchondylar notch of the distal femur with a sharp-pointed gimlet and a hole having the diameter of 3 mm and depth of 3 mm is made centering around the scar with a drill. A punch having the diameter of 3 mm may be used for the same region, and the fall thickness cartilage defect is created. The damaged region is observed 3-4 months after the cartilage damage is induced as in the above. And it is confirmed that the damaged region of cartilage is not cured by itself.

In the meantime, 0.25 ml of the composition of the present invention manufactured in the third step is injected and pushed into the damaged region of cartilage of a rabbit by using a syringe.

Thereafter, the knee cap is returned to its original position, soft tissues around the knee cap are repaired with absorbable sutures, and the skin is closed with non-absorbable sutures. The leg on the opposite side is regarded to be a control group, into which only biodegradable polymers are applied.

After it is confirmed that the rabbit regains consciousness from anesthesia, it is allowed to move freely, and antibiotics are administered to it in order to prevent infection after the operation until the next day. After 11 weeks, sections of the articular cartilage region of each rabbit which were subject to damage and treated are obtained and inspected for newly formed cartilage. The results of comparison are shown in FIGS. 2a and 2b.

As shown in FIGS. 2a and 2b, the total thickness of repaired layers produced newly after the composition of the present invention is applied is shown to be more than twice greater (FIG. 2b) than that when only the polymer is applied (FIG. 2b).

FIGS. 2a and 2b are amplified and shown in FIGS. 3a and 3b in order to compare the property of newly formed cartilage repair tissue. As shown in FIGS. 3a and 3b, cartilage tissue of the almost same appearance as that of original normal outside cartilage tissue (right side) are produced newly (left side) if the composition of the present invention is applied (FIG. 3b), although the cellular density is greater than that of original normal cartilage tissues. On the other hand, if only the polymer is applied (FIG. 3a), the shape of cells is rough compared to that of normal cells and the density is shown to be low.

Accordingly, it is seen that the composition of the present invention is able to produce cartilage tissue in the damaged region of articular cartilage with a superior efficiency and to treat the articular cartilage damage effectively.

In conclusion, the composition for the treatment of articular cartilage damage of the present invention shows excellent effects in histologic aspects for the treatment of the cartilage damage. Compared to the conventional methods of treatment of the articular cartilage damage, the method of its treatment using the composition of the present invention is able to reduce the time, efforts, and expenses for the treatment of articular cartilage damage since the subject method has an effect of sufficiently repairing the articular cartilage damage by employing simple procedures such as the arthroscopic operation or much simpler operation.

While the invention has been described in terms of a single preferred embodiment, those skilled in the art will recognize that the invention can be practiced with modification within the spirit and scope of the appended claims.

What is claimed is:

1. A composition for the treatment of articular cartilage damage, loss, or defect, said composition comprising mesenchymal stem cells isolated from umbilical cord blood, a culture medium, and a biocompatible polymer,
    wherein said composition treats articular cartilage damage, loss, or defect when administered to a site of articular cartilage damage, loss, or defect in a subject.

2. The composition for the treatment of articular cartilage damage of claim 1, wherein the cellular component is contained in an amount of $1 \times 10^6$ to $5 \times 10^7$ cells in 1 ml of the composition.

3. The composition for the treatment of articular cartilage damage of claim 1, wherein said biocompatible polymer biodegrades.

4. The composition for the treatment of articular cartilage damage of claim 3, wherein said biocompatible polymer is at least one selected from the group consisting of natural polymers and synthetic polymers comprised of hydroxy acids.

5. The composition for the treatment of articular cartilage damage of claim 4, wherein said biocompatible polymer is at least one selected from the group consisting of fibrin, gelatin, collagen, hyaluronic acid, polyphosphazine, polyacrylate, polyglactic acid, polyglycolic acid, pluronic acid, alginic acid, and their salts.

6. The composition for the treatment of articular cartilage damage of claim 5, wherein said biocompatible polymer further comprises a chitosan.

7. The composition for the treatment of articular cartilage damage of claim 5, wherein said biocompatible polymer is pluronic acid in a final concentration of 30% by weight based on the total volume of the composition.

8. The composition for the treatment of articular cartilage damage of claim 5, wherein said biocompatible polymer is the hyaluronic acid in a final concentration of 3-4% by weight based on the total volume of the composition.

9. The composition for the treatment of articular cartilage damage of claim 5, wherein said biocompatible polymer is pluronic acid in a final concentration of 15-30% by weight and hyaluronic acid in a final concentration of 2-4% by weight, each based on the total volume of the composition.

10. The composition for the treatment of articular cartilage damage of claim 9, wherein said biocompatible polymer further comprises chitosan.

11. The composition for the treatment of articular cartilage damage of claim 3, wherein the said composition contains $1 \times 10^6$ to $5 \times 10^7$ cells per mL of the composition.

12. The composition for the treatment of articular cartilage damage of claim 4, wherein said composition contains $1 \times 10^6$ to $5 \times 10^7$ cells per mL of the composition.

13. The composition for the treatment of articular cartilage damage of claim 5, wherein said composition contains $1 \times 10^6$ to $5 \times 10^7$ cells per mL of the composition.

14. The composition for the treatment of articular cartilage damage of claim 6, wherein said composition contains $1 \times 10^6$ to $5 \times 10^7$ cells per mL of the composition.

15. The composition for the treatment of articular cartilage damage of claim 7, wherein said composition contains $1 \times 10^6$ to $5 \times 10^7$ cells per mL of the composition.

16. The composition for the treatment of articular cartilage damage of claim 8, wherein said composition contains $1 \times 10^6$ to $5 \times 10^7$ cells per mL of the composition.

17. The composition for the treatment of articular cartilage damage of claim 9, wherein said composition contains $1 \times 10^6$ to $5 \times 10^7$ cells per mL of the composition.

18. The composition for the treatment of articular cartilage damage of claim 10, wherein said composition contains $1 \times 10^6$ to $5 \times 10^7$ cells per mL of the composition.

19. The composition for the treatment of articular cartilage damage of claim 4 wherein said natural polymer is a protein or polysaccharide.

20. A method for treatment of articular cartilage damage, loss, or defect in a subject in need thereof comprising administering the composition of claim 1 to a site of articular cartilage damage, loss, or defect in said subject.

21. A method for treatment of articular cartilage damage, loss, or defect in a subject in need thereof comprising administering the composition of claim 2 to a site of articular cartilage damage, loss, or defect in said subject.

22. A method for treatment of articular cartilage damage, loss, or defect in a subject in need thereof comprising administering the composition of claim 3 to a site of articular cartilage damage, loss, or defect in said subject.

23. A method for treatment of articular cartilage damage, loss, or defect in a subject in need thereof comprising administering the composition of claim 4 to a site of articular cartilage damage, loss, or defect in said subject.

24. A method for treatment of articular cartilage damage, loss, or defect in a subject in need thereof comprising administering the composition of claim 5 to a site of articular cartilage damage, loss, or defect in said subject.

25. A composition for the treatment of articular cartilage damage, loss, or defect, said composition comprising mesenchymal stem cells isolated from umbilical cord blood, a culture medium, and a biocompatible polymer,
   wherein the composition contains $1 \times 10^6$ to $5 \times 10^7$ cells per mL of the composition;
   wherein the biocompatible polymer is hyaluronic acid in a final concentration of 0.5%-4% by weight based on the total volume of the composition; and
   wherein said composition treats articular cartilage damage, loss, or defect when administered to a site of articular cartilage damage, loss, or defect in a subject.

26. The composition of claim 25, wherein the final concentration of hyaluronic acid is 1-4% by weight based on the total volume of the composition.

27. The composition of claim 25, wherein the final concentration of hyaluronic acid is 1.5-4% by weight based on the total volume of the composition.

28. The composition of claim 25, wherein the final concentration of hyaluronic acid is 2-4% by weight based on the total volume of the composition.

29. The composition of claim 1, which is an injectable formulation.

30. The composition of claim 3, which is an injectable formulation.

31. The composition of claim 4, which is an injectable formulation.

32. The composition of claim 5, which is an injectable formulation.

33. The composition of claim 25, which is an injectable formulation.

\* \* \* \* \*

UNITED STATES PATENT AND TRADEMARK OFFICE
CERTIFICATE OF CORRECTION

PATENT NO. : 7,459,307 B2
APPLICATION NO. : 10/485816
DATED : December 2, 2008
INVENTOR(S) : Chul-Won Ha et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (235) days Delete the phrase "by 235 days" and insert -- by 285 days --

Signed and Sealed this

Seventh Day of July, 2009

JOHN DOLL
*Acting Director of the United States Patent and Trademark Office*